(12) United States Patent
Stolen et al.

(10) Patent No.: US 9,227,071 B2
(45) Date of Patent: Jan. 5, 2016

(54) SYSTEMS AND METHODS FOR SETTING PARAMETERS OF IMPLANTABLE MEDICAL DEVICES USING PREDICTIVE MARKER DATA

(75) Inventors: Craig M. Stolen, New Brighton, MN (US); Harlan Bos, Stillwater, MN (US); Timothy E. Meyer, North Oaks, MN (US); Arjun Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 857 days.

(21) Appl. No.: 13/536,526

(22) Filed: Jun. 28, 2012

(65) Prior Publication Data

US 2013/0046196 A1 Feb. 21, 2013

Related U.S. Application Data

(60) Provisional application No. 61/503,121, filed on Jun. 30, 2011.

(51) Int. Cl.
*A61N 1/365* (2006.01)
*G01N 33/74* (2006.01)

(52) U.S. Cl.
CPC ............ *A61N 1/36557* (2013.01); *G01N 33/74* (2013.01); *G01N 2333/5754* (2013.01); *G01N 2800/326* (2013.01)

(58) Field of Classification Search
CPC ........ A61B 6/00; A61B 5/0452; A61N 1/365; A61N 1/36557
USPC .................................................. 600/436, 515
See application file for complete search history.

(56) References Cited

U.S. PATENT DOCUMENTS

| 4,562,841 A | 1/1986 | Brockway et al. |
| 7,764,995 B2 | 7/2010 | Girouard et al. |

(Continued)

FOREIGN PATENT DOCUMENTS

| EP | 2726147 | 5/2014 |
| JP | 2014521402 | 8/2014 |
| WO | 2013003604 | 1/2013 |

OTHER PUBLICATIONS

"PCT International Search Report and Written Opinion", International Application No. PCT/US20121044669, corresponding to, mailed Sep. 19, 2012, pp. 1-13.
"Communication Pursuant to Article 94(3) EPC," for European Patent Application No. 12733574.3, mailed on Feb. 25, 2015 (5 pages).
"Communication Pursuant to Rules 161(1) and 162 EPC," for European Patent Application No. 12733574.3, mailed Mar. 28, 2014 (2 pages).

(Continued)

*Primary Examiner* — Catherine Voorhees
*Assistant Examiner* — Roland Dinga
(74) *Attorney, Agent, or Firm* — Pauly, DeVries, Smith & Deffner, L.L.C.

(57) ABSTRACT

Embodiments of the invention are related to systems and methods for setting parameters of implantable medical devices, amongst other things. In an embodiment, the invention includes a method for programming an implantable medical device including sensing concentrations of a predictive marker such as ET-1 in a patient, selecting programming parameter values based on the sensed concentrations of the predictive marker, and implementing the selected programming parameter values. In an embodiment the invention includes a method for detecting arrhythmia in a patient including sensing concentrations of the predictive marker in a patient, selecting a level of stringency to be used in an arrhythmia detection module based on the sensed concentrations of the predictive marker, sensing electrical signals in the patient, and evaluating the sensed electrical signals for indicia of an arrhythmia using the arrhythmia detection module. Other embodiments are also included herein.

10 Claims, 6 Drawing Sheets

(56) References Cited

U.S. PATENT DOCUMENTS

| | | | |
|---|---|---|---|
| 2005/0004476 A1 | 1/2005 | Payvar et al. | |
| 2006/0111746 A1* | 5/2006 | Foreman | A61N 1/36114 607/2 |
| 2007/0270675 A1 | 11/2007 | Kane et al. | |
| 2008/0058642 A1* | 3/2008 | Gould | A61B 5/02007 600/436 |
| 2008/0288009 A1 | 11/2008 | Kim et al. | |
| 2010/0204744 A1 | 8/2010 | Shuros et al. | |
| 2011/0295084 A1 | 12/2011 | Thakur et al. | |

OTHER PUBLICATIONS

"International Preliminary Report on Patentability," for PCT/US2012/044669, mailed Jan. 16, 2014 (8 pages).

"Response to Communication Pursuant to Article 94(3) EPC," for European Patent Application No. 12733574.3, mailed Feb. 25, 2015 and filed with the EPO Apr. 13, 2015 (10 pages).

"Response to Communication Pursuant to Rules 161(1) and 162 EPC," for European Patent Application No. 12733574.3, mailed Mar. 28, 2014 and filed with the EPO on Oct. 6, 2014 (9 pages).

* cited by examiner

SYSTEMS AND METHODS FOR SETTING PARAMETERS OF IMPLANTABLE MEDICAL DEVICES USING PREDICTIVE MARKER DATA

This application claims the benefit of U.S. Provisional Application No. 61/503,121, filed Jun. 30, 2011, the contents of which are herein incorporated by reference.

TECHNICAL FIELD

This disclosure relates generally to implantable medical devices, and more particularly, to systems and methods for setting parameters of implantable medical devices, amongst other things.

BACKGROUND OF THE INVENTION

Implantable medical devices (IMDs) are commonly used to provide treatment to patients. Implantable medical devices can include cardiac rhythm management devices and neurological stimulation devices, amongst others.

Some types of implantable medical devices deliver electrical stimuli to a target tissue via a lead wire ("stimulation lead") or catheter having one or more electrodes disposed in or about the target tissue. In the context of cardiac rhythm management devices, the electrical stimuli can be delivered in the form of pacing pulses to pace the heart and/or relatively high energy defibrillation shocks or cardioversion shocks to terminate arrhythmias.

However, in some instances, a device may deliver a shock to a patient even when that patient is not experiencing a potentially dangerous arrhythmia. See, e.g., Spragg, *Heart Rhythm*, 5(5):762-765 (May 2008). This can be due to the device erroneously sensing the presence of an arrhythmia, which can in turn be the result of the inherent difficulties of accurately sensing cardiac activity and also a desire to value patient safety over patient comfort. However, unnecessary shocks can cause patient distress and can deplete battery life, amongst other things.

Endothelin-1 (ET-1) is a vasoconstricting peptide produced primarily in the endothelium. In addition to its role in vasoconstriction, ET-1 also plays a role in exerting bronchoconstriction and vascular and airway cell proliferation, via $ET_A$ and $ET_B$ receptors.

SUMMARY OF THE INVENTION

Embodiments of the invention are related to systems and methods for setting parameters of implantable medical devices, amongst other things. In an embodiment, the invention includes a method for programming an implantable medical device including sensing concentrations of a predictive marker such as ET-1 in a patient, selecting programming parameter values based on the sensed concentrations of the predictive marker, and implementing the selected programming parameter values.

In an embodiment the invention includes a method for detecting arrhythmia in a patient including sensing concentrations of a predictive marker such as ET-1 in a patient, selecting a level of stringency to be used in an arrhythmia detection module based on the sensed concentrations of the predictive marker, sensing electrical signals in the patient, and evaluating the sensed electrical signals for indicia of an arrhythmia using the arrhythmia detection module.

In an embodiment, the invention includes an implantable medical device including a processor and a memory circuit operatively coupled to the processor. The implantable medical device can be configured to sense electrical signals in a patient and evaluate the sensed electrical signals for indicia of an arrhythmia in view of the predictive marker concentration data regarding the patient.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Many implantable medical devices are capable of being programmed in order to control the way in which they provide therapy to a given patient. Programming generally occurs through the process of setting parameter values that influence the functioning of the device. At a basic level, parameters can include such things as pacing amplitude, pacing rate, and pulse width. At a higher level, parameters can also control device operation by affecting the detection of arrhythmias, the therapeutic response to arrhythmias, and the like. Frequently, values for parameters are set by a clinician.

As described above, unnecessary shocks can cause patient distress and can deplete battery life of an implanted device.

In accordance with embodiments herein, concentration data regarding predictive markers can be used in order to set values for various programming parameters. Concentration data regarding predictive markers can be used to gauge the risk that a patient will undergo an adverse arrhythmic event and can thereby be used to set values for various programming parameters in a manner that will reduce the incidence of unnecessary shocks. As a specific example, the concentration of ET-1 can be used to gauge the risk that a patient will undergo an adverse arrhythmic event and can be used to set values for programming parameters.

As used herein, reference to "ET-1" shall include, unless the context dictates otherwise, the 212 amino acid precursor (SEQ ID NO: 1) sometimes referred to as "pre-proET-1", the 38 amino acid endothelin-1 precursor (SEQ ID NO: 2) sometimes referred to as "bigET-1", the 21 amino acid ET-1 molecule (SEQ ID NO: 3), the 45 amino acid pre-proET-1 C terminal fragment (SEQ ID NO: 4) representing amino acids 168-212 of pre-proET-1 and referred to as "CT-proET-1", and fragments of these.

TABLE 1

```
  1 MDYLLMIFSL LFVACQGAPE TAVLGAELSA VGENGGEKPT
    PSPPWRLRRS

51 KRCSCSSLMD KECVYFCHLD IIWVNTPEHV VPYGLGSPRS
    KRALENLLPT

101 KATDRENRCQ CASQKDKKCW NFCQAGKELR AEDIMEKDWN
    NHKKGKDCSK

151 LGKKCIYQQL VRGRKIRRSS EEHLRQTRSE TMRNSVKSSF
    HDPKLKGNPS

201 RERYVTHNRA HW
    (SEQ ID NO 1)
```

TABLE 2

```
  1  CSCSSLMDKE CVYFCHLDII WVNTPEHVVP YGLGSPRS
     (SEQ ID NO 2)
```

TABLE 3

```
  1  CSCSSLMDKE CVYFCHLDII W    (SEQ ID NO 3)
```

TABLE 4

```
  1  RSSEEHLRQT RSETMRNSVK SSFHDPKLKG NPSRERYVTH
     NRAHW
     (SEQ ID NO 4)
```

In accordance with various embodiments herein, data regarding concentrations of predictive markers, such as ET-1, can be used to modulate the determination of whether or not an arrhythmia is taking place. In various embodiments, data regarding concentrations of predictive markers can be used to modulate the determination of whether or not therapy, such as in the form of an electrical shock, should be administered. In this manner, patients who are not at a substantial risk of developing an arrhythmia will be less likely to receive therapy when it is not needed. Conversely, patients who are at a substantial risk of developing an arrhythmia will be more likely to receive therapy when it is appropriate.

Figure 1:
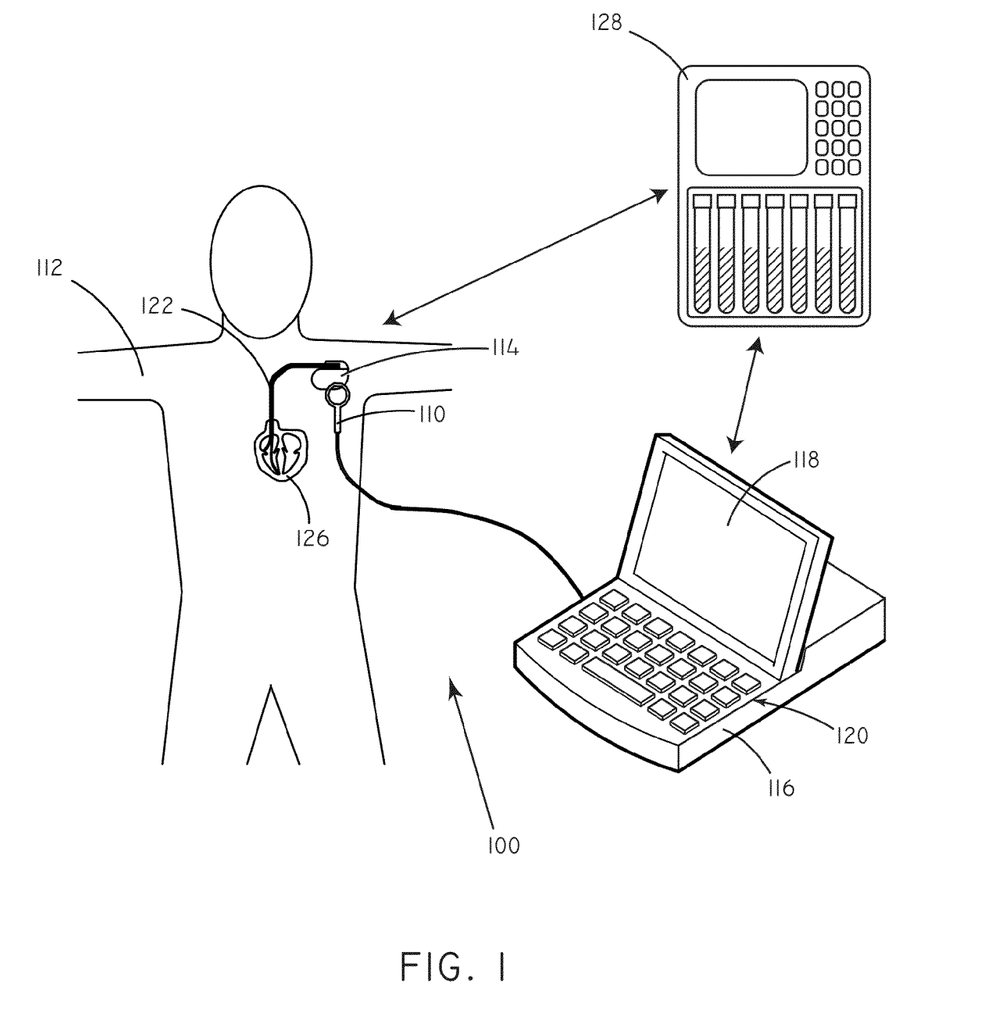
FIG. 1 is a schematic of an exemplary system consistent with at least one embodiment of the invention.

FIG. 1 is a schematic view of an exemplary system 100, consistent with at least one embodiment of the invention. The system 100 can include an implantable medical device 114 disposed within a patient 112. The implantable medical device 114 can be of various types such as, for example, a pacemaker, a cardioverter-defibrillator, a cardiac resynchronization device, or the like. One example of an implantable medical device is disclosed in commonly assigned U.S. Pat. No. 4,562,841, the content of which is herein incorporated by reference in its entirety. In some embodiments, the implantable medical device 114 can include one or more leads 122 disposed in or near the patient's heart 126.

The implantable medical device 114 can be in communication with an external medical device 116. In some embodiments, communication between the implantable medical device 114 and the external medical device 116 can be via inductive communication through a wand 110 held on the outside of the patient 112 near the implantable medical device 114. However, in other embodiments, communication can be carried out via radiofrequency transmission, acoustically, or the like.

The external medical device 116 can include a video output device, such as a display screen 118 for displaying video output. In some embodiments, the external medical device 116 can be configured to process the gathered data. The external medical device 116 can also include a user input device 120, such as keys. The external medical system 116 can be for example, a programmer/recorder/monitor device, a computer, an advanced patient management system, or a personal digital assistant (PDA). Exemplary programmer/recorder/monitor devices include the Model 3120 Programmer, available from Boston Scientific Corporation, Natick, Mass.

In some embodiments the implantable medical device 114 can include one or more implantable sensors in order to gather data regarding the patient 112. By way of example, the medical device 114 can include an implantable sensor in order to sense concentrations of a predictive marker. In some embodiments, the implantable sensor can sense concentrations of ET-1 in vivo. Exemplary implantable sensors are described in U.S. Publ. Pat. Appl. No. 2007/0270675, the content of which is herein incorporated by reference in its entirety.

In some embodiments, concentrations of predictive markers can be measured using an in vitro assay. By way of example, in some embodiments, an external assay device 128 can be used to measure concentrations of a predictive marker such as ET-1. The patient 112 can provide an assayable quantity of blood or other bodily fluid to the external assay device 128 and the device can measure the amount of the predictive marker present and then report back regarding concentration data either directly to the implantable medical device 114 or through the external medical device 116. It will be appreciated that various assays for predictive markers are known to those of skill in the art and are available commercially.

Figure 2:
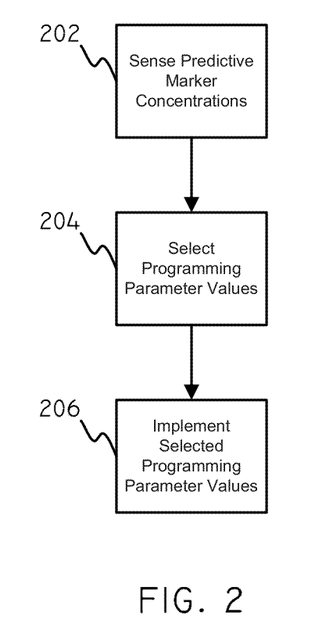
FIG. 2 is a flow chart of an exemplary method consistent with at least one embodiment of the invention.

Referring now to FIG. 2, a flow chart of an exemplary method is shown. Aspects of this method can be executed by an implantable medical device, an external medical device or both. In accordance with various embodiments herein, predictive marker levels within a patient can be sensed or otherwise determined in an operation 202. In some embodiments this can be done with an implantable chemical sensor capable of detecting predictive marker concentrations. In other embodiments, this can be accomplished using an in vitro assay. In some embodiments, predictive marker concentrations can be determined by a care provider and then input into an implantable medical device or an external medical device.

Concentrations of predictive markers can be sensed one or more times. In some embodiments, concentrations of a predictive marker can be sensed a plurality of times over a given time period. By way of example, concentrations of a predictive marker can be sensed a plurality of times over a time period greater than or equal to one month. In some embodiments concentrations of a predictive marker can be sensed on a preset schedule. For example, in some embodiments concentrations of a predictive marker can be measured at approximately the same time on each day that the predictive marker is measured so as to control for circadian variations in predictive marker concentrations. In some embodiments concentrations of one or more predictive markers can be measured in response to a command from a clinician or from a separate system.

In another operation 204 parameter values can be selected in view of predictive marker concentrations for one or more parameters. Predictive marker concentrations can be actionable either as a magnitude from a discrete measurement event, as an average magnitude from a plurality of measurement events, or as part of a concentration trend over time. In some embodiments, predictive marker concentrations can be actionable in conjunction with other data, such as data regarding concentrations of other analytes of interest. Other analytes of interest can include creatinine kinase, troponin, electrolytes such as potassium, sodium, calcium, and the like.

In some embodiments, selecting parameter values can include an operation of assessing the risk of arrhythmic events for the patient based on sensed concentrations of a predictive marker. In various embodiments, risk to the patient, as judged at least in part by the predictive marker concentration data, can be classified into risk categories for purposes of device operation. In some embodiments, the patient can be classified as either high risk or normal risk with regard to arrhythmic events. In some embodiments, the patient can be classified as either high risk, normal risk, or low risk with regard to arrhythmic events, based at least in part on predictive marker concentrations.

In some embodiments, risk to the patient can be classified into between 2 and n risk categories. In some embodiments, there are between 2 and 12 risk categories. In some embodiments, there are 3 risk categories. It will be appreciated the specific number of risk categories can vary depending on various factors including the desired level of granularity.

In many embodiments, parameter values can be selected so that patients who are at high risk for arrhythmic events are more likely to receive therapy than are patients who are at low risk for arrhythmic events. As such, in some embodiments, patients who are at high risk for arrhythmic events can be evaluated with less stringency in terms of what set of indicia is necessary to conclude that a patient is experiencing an arrhythmia. A patient who is evaluated with less stringency is more likely to receive therapy. Conversely, in some embodiments, patients who are at low risk for arrhythmic events can be evaluated with greater stringency in terms of what set of indicia is necessary to conclude that a patient is experiencing an arrhythmia. A patient who is evaluated with greater stringency is less likely to receive therapy.

Parameter values can be selected from amongst a plurality of possible values for many different parameters. Exemplary parameters can include, but are not limited to, rate discrimination settings, rhythm morphology settings, and rhythm duration settings. In some embodiments, rate discrimination settings can be lowered if the patient is categorized as having a high or above average risk of arrhythmic events. For example, the heart rate threshold to delineate between ventricular fibrillation and ventricular tachycardia can be lowered, making it more likely that the patient will receive therapy to treat ventricular fibrillation. As another specific example, the rhythm duration settings can be lowered if the patient is categorized as having a high or above average risk of arrhythmic events. For example, the amount of time that a patient must experience a heart rate above a certain level before the device initiates therapeutic intervention can be reduced if the patient is categorized as having a high or above average risk of arrhythmic events.

In another operation 206, the selected parameter values can be implemented by setting the implantable medical device to utilize the selected parameter values for controlling aspects of ongoing device operation. In some embodiments, this can be accomplished through an exchange of data between an external medical device and an internal medical device. In other embodiments, this can be executed by the implantable medical device itself as it changes its operation to utilize the selected parameter values.

Figure 3:
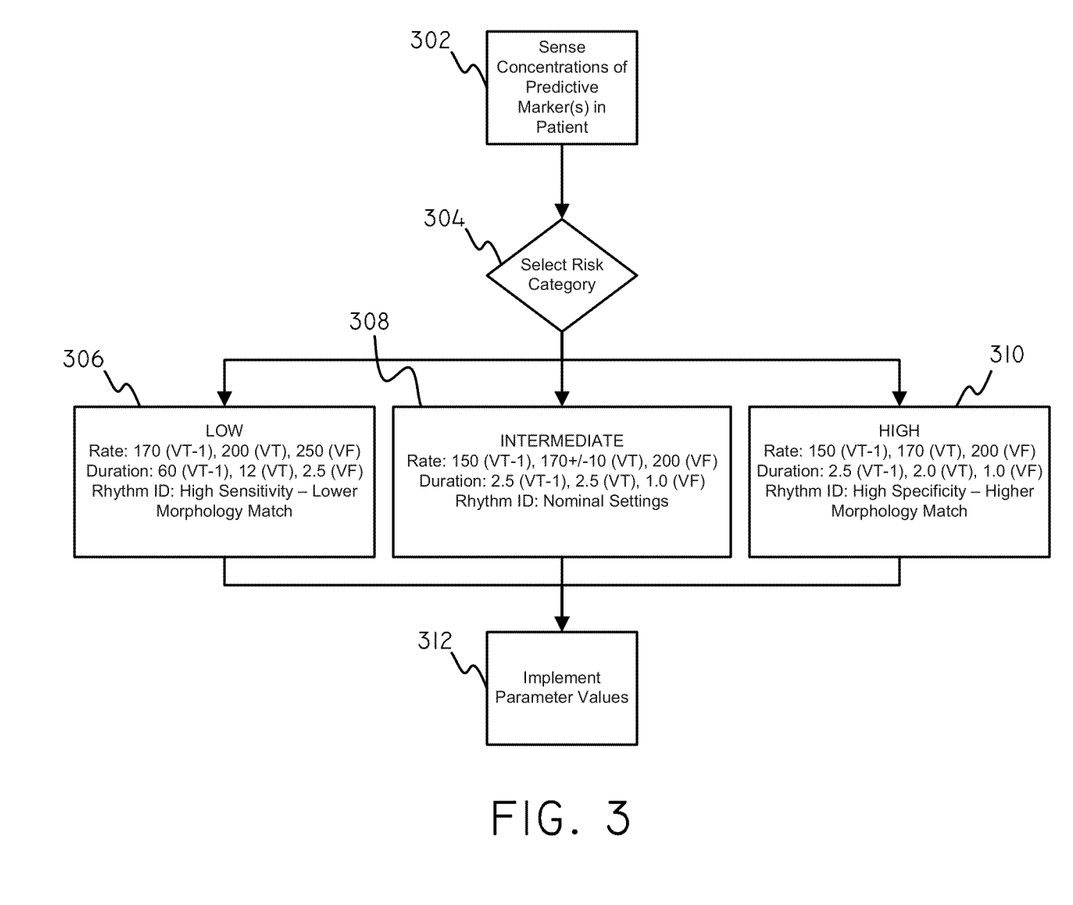
FIG. 3 is a flow chart of an exemplary method consistent with at least one embodiment of the invention.

Referring now to FIG. 3, a flow chart of a method is shown in accordance with an embodiment. Predictive marker levels within a patient can be sensed or otherwise determined in an operation 302. In some embodiments this can be done with an implantable chemical sensor capable of detecting predictive marker concentrations. In other embodiments, this can be accomplished using an in vitro assay. In some embodiments, predictive marker concentrations can be determined by a care provider and then input into an implantable medical device or an external medical device.

In another operation 304, a risk category can be selected for the patient. As described previously, the specific number of risk categories can vary. However, in this specific illustration, three risk categories are utilized: low 306, intermediate 308, and high 310. One example of specific concentrations of ET-1, and more specifically CT-proET-1, used to delineate between risk categories is illustrated in Table 1 below.

TABLE 1

| LOW RISK | INTERMEDIATE RISK | HIGH RISK |
| --- | --- | --- |
| <65 pmol/L | 65-100 pmol/L | >100 pmol/L |
| <66.6 pmol/L | 66.6-104 pmol/L | >104 pmol/L |

It will be appreciated that the specific delineation between categories based on CT-proET-1 concentrations shown in Table 1 is provided by way of illustration only and should not be considered to limit the scope included herein. In some embodiments, the concentration of ET-1 for delineating between low risk and intermediate risk can be between 55 and 75 pmol/L. In some embodiments, the concentration of ET-1 for delineating between low risk and intermediate risk can be between 60 and 70 pmol/L. In some embodiments, the concentration of ET-1 for delineating between intermediate risk and high risk can be between 90 and 110 p/molL. In some embodiments, the concentration of ET-1 for delineating between intermediate risk and high risk can be between 95 and 105 pmol/L.

In this example, using the first values from the table, if the concentration of CT-proET-1 is less than 65 pmol/L, then the low risk category can be selected. In response to this category assignment, various parameter values can be selected. One exemplary parameter is rate discrimination settings. Tachycardia can be defined as a heart rate (or R to R frequency) of greater than 100 beats per minute. However, rate discrimination settings can be used to distinguish between different categories of tachycardia for purposes of treatment. Exemplary categories of tachycardia can include VT-1 (a less severe ventricular tachycardia), VT (ventricular tachycardia), and VF (ventricular fibrillation). The precise cut-off values (or threshold value) to distinguish between different categories of tachycardia can be altered based on the assigned risk category.

Table 2 below provides an example of how threshold values for discriminating between different categories of arrhythmia can be changed as a result of assignment of the patient to a particular risk classification. In accordance with the example of Table 2, if the patient is classified as low risk, then the patient can be considered to be in the ventricular fibrillation category if the patient's sensed heart rate is greater than 250 beats per minute. However, if the patient is classified as high risk, then the threshold for VF can be lowered. For example, if the patient is classified as high risk then the patient can be considered to be in the ventricular fibrillation category if the patient's sensed heart rate is greater than 200 beats per minute. It will be appreciated that threshold values provided in Table 2 are just provided for purposes of illustration and that in various embodiments the specific threshold values can differ.

TABLE 2

| ARRHYTHMIA CATEGORY | LOW RISK | INTERMEDIATE RISK | HIGH RISK |
|---|---|---|---|
| VT-1 | >170 BPM | >150 BPM | >150 BPM |
| VT | >200 BPM | >170 +/− 10 BPM | >170 BPM |
| VF | >250 BPM | >200 BPM | >200 BPM |

Another exemplary parameter is arrhythmia duration. Arrhythmia duration values can control how long a device observes arrhythmic heart behavior before initiating further action, such as the administration of therapy. Arrhythmia duration values should be set to be sufficiently long so that merely spurious sensed electrical activity does not result in the administration of therapy that may not be necessary. However, arrhythmia duration values should be set to be short enough that the device does not wait longer than is necessary to administer therapy that is needed. By utilizing data, such as predictive marker concentration data, these times can be effectively tuned to an optimal value.

Exemplary values for arrhythmia duration, as selected based on risk classification, are shown in Table 3 below. By way of example, if the patient is classified as low risk, then the required time before action is taken in the ventricular fibrillation (VF) category can be set to 2.5 seconds. However, if the patient is classified as high risk, then the arrhythmia duration time can be reduced. For example, if the patient is classified as high risk, then the arrhythmia duration time for the ventricular fibrillation (VF) category can be set to 1.0 seconds. It will be appreciated that these specific values are provided by way of illustration only and do not serve to limit the scope of embodiments herein.

TABLE 3

| ARRHYTHMIA CATEGORY | LOW RISK | INTERMEDIATE RISK | HIGH RISK |
|---|---|---|---|
| VT-1 | 60 seconds | 2.5 seconds | 2.5 seconds |
| VT | 12 seconds | 2.5 seconds | 2.0 seconds |
| VF | 2.5 seconds | 1.0 seconds | 1.0 seconds |

Another possible parameter is rhythm morphology discrimination settings. Rhythm morphology can be used to distinguish between different types of tachyarrhythmias. By way of example, ventricular fibrillation generally exhibits a different morphology of sensed electrical activity than a supraventricular tachycardia. However, ventricular tachycardia and supraventricular tachycardias may have lesser differences in morphology of sensed electrical activity making it difficult for a device with fixed parameters to be both specific and sensitive in its therapy.

Morphology-based approaches for discriminating between different categories of arrhythmias can include comparing the morphological shape of a cardiac depolarization to a template morphology in order to classify a heart beat or heart rhythm. In the comparison process, a correlation value can be determined (e.g., a feature correlation coefficient (FCC)) that can provide an indication of a degree of similarity between the shape of a depolarization being examined and the shape of the template to which it is compared. The correlation value can then be compared to a correlation threshold value in order to classify the rhythm. Further aspects of morphology based discrimination approaches are described in U.S. Publ. Pat. App. No. 2008/0288009, the content of which is herein incorporated by reference.

Knowledge of predictive marker data can be used to adjust rhythm morphology discrimination settings. For example, if ET-1 levels are used to classify a patient as low risk for ventricular tachycardia, then a lower morphology match may be selected, so that a patient is less likely to receive inappropriate therapy for a supraventricular tachycardia. Conversely, if the patient has a high risk of ventricular tachycardia based on the ET-1 level, then a higher morphology match is selected to ensure appropriate therapy for a ventricular tachycardia that may occur. Table 4 describes exemplary values with the morphology match in this example showing potential quantitative values for the feature correlation coefficient (FCC) match which is one manifestation of how the morphology match can be computed.

TABLE 4

| LOW RISK | INTERMEDIATE RISK | HIGH RISK |
|---|---|---|
| Higher Specificity - Lower Morphology Match FCC = 70-93% | Nominal Settings FCC = 94% | Higher Sensitivity - Higher Morphology Match FCC = 95-96% |

In another operation 312, the selected parameter values can be implemented by setting the implantable medical device to utilize the selected parameter values for controlling aspects of ongoing device operation. In some embodiments, this can be accomplished through an exchange of data between an external medical device and an internal medical device. In other embodiments, this can be executed by the implantable medical device itself as it changes its operation to utilize the selected parameter values.

Figure 4:
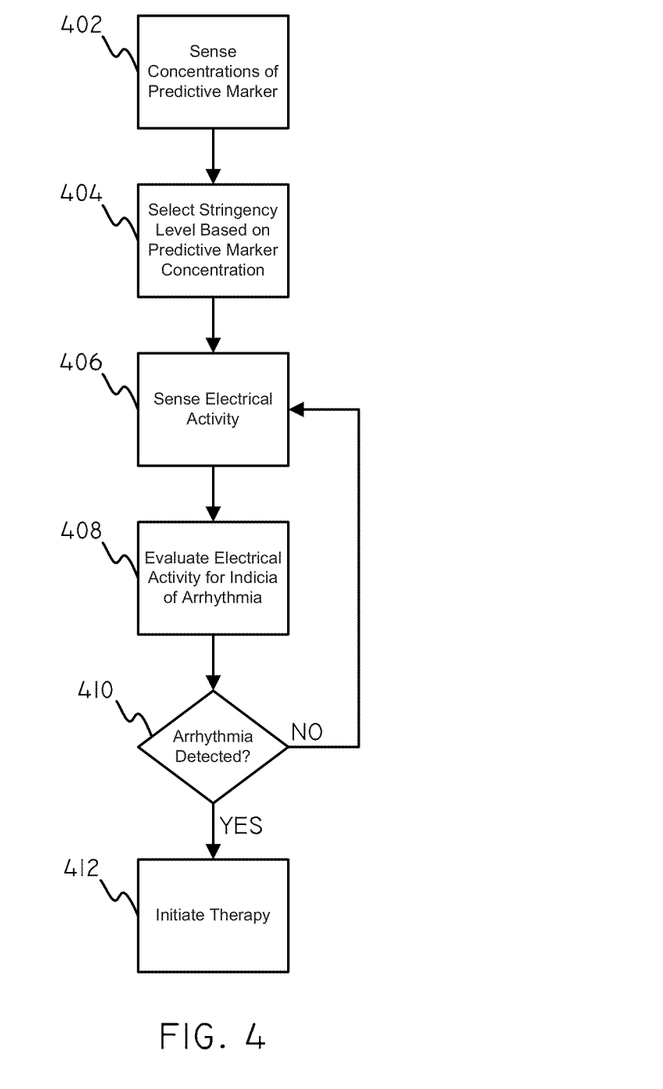
FIG. 4 is a flow chart of an exemplary method consistent with at least one embodiment of the invention.

Referring now to FIG. 4, a flow chart of a method is shown in accordance with an embodiment. Predictive marker levels within a patient can be sensed or otherwise determined in an operation 402. In some embodiments this can be done with an implantable chemical sensor capable of detecting predictive marker concentrations. In other embodiments, this can be accomplished using an in vitro assay. In some embodiments, predictive marker concentrations can be determined by a care provider and then input into an implantable medical device or an external medical device.

In another operation 404, a stringency level can be selected. The specific number of stringency levels can vary. However, in this specific illustration, three stringency categories are utilized: low, intermediate, and high. Examples of specific concentrations of ET-1 used to delineate between stringency levels is illustrated in Table 5 below.

TABLE 5

| HIGH STRINGENCY | INTERMEDIATE STRINGENCY | LOW STRINGENCY |
|---|---|---|
| <65 pmol/L | 65-100 pmol/L | >100 pmol/L |
| <66.6 pmol/L | 66.6-104 pmol/L | >104 pmol/L |

It will be appreciated that the specific delineation between stringency levels based on ET-1 concentrations shown in Table 5 is provided by way of illustration only and should not be considered to limit the scope included herein. In some embodiments, the concentration of ET-1 for delineating between high stringency and intermediate stringency can be between 55 and 75 pmol/L. In some embodiments, the concentration of ET-1 for delineating between high stringency and intermediate stringency can be between 60 and 70 pmol/L. In some embodiments, the concentration of ET-1 for delineating between intermediate stringency and low stringency can be between 90 and 110 p/molL. In some embodiments, the concentration of ET-1 for delineating between intermediate stringency and low stringency can be between 95 and 105 pmol/L.

In another operation 406, intrinsic electrical activity of a patient can be sensed. Sensing can be performed using implantable electrodes with a unipolar or bipolar configuration. Beyond electrodes, the system can include a sensing amplifier as well as other circuitry to facilitate the sensing of intrinsic electrical activity.

In another operation 408, the sensed electrical activity can be evaluated for indicia of arrhythmia, in view of the stringency level assigned in operation 404. The system can, for example, use the sensed electrical activity and calculate various data points that can serve as indicia such as R to R frequency, R to R frequency variance, waveform morphology, cardiac output, and the like. If the stringency level is low, then the device will be more likely to conclude that indicia of arrhythmia are present. However, if the stringency level is high, then the device will be less likely to conclude that indicia of arrhythmia are present.

In another operation, the system can evaluate whether or not arrhythmia has been detected, and, if so, what type of arrhythmia it is. If there is no arrhythmia detected, then the system can return to sensing electrical activity. However, if an arrhythmia has been detected, then in another operation 412, therapy can be administered. Therapy can include electrical stimulation pulses at various magnitudes including, but not limited to, anti-tachycardia pacing, defibrillation shocks, cardioversion shocks, and the like. In some embodiments, multiple therapy types are attempted. For example, in some circumstances anti-tachycardia pacing may be attempted first, followed by one or more defibrillation shocks. The choice of which therapy to administer can be influenced by the risk level of the patient as classified, at least in part, by the concentration of predictive marker within the patient. By way of example, the system can be configured to be quicker to administer more aggressive therapy, such as a defibrillation shock, rather than anti-tachycardia pacing, if the patient has been determined to be at a high risk of suffering an arrhythmic event.

Devices and Systems

Figure 5:
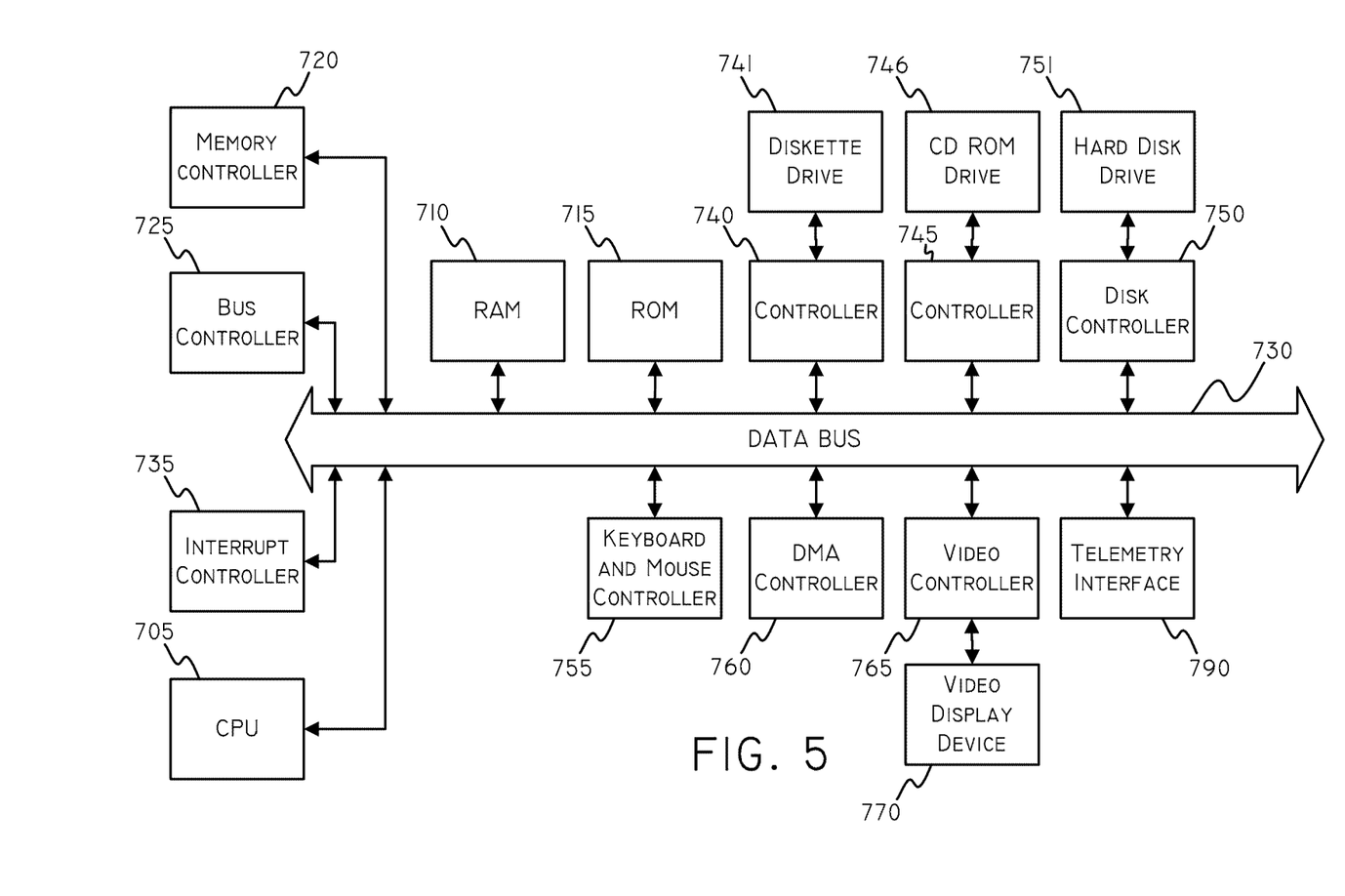
FIG. 5 is a schematic diagram of various component of an external device in accordance with some embodiments of the invention.

In some embodiments, one or more operations described above can be executed by an external device. Exemplary external devices, such as programmer/recorder/monitors, can include components common to many computing devices. Referring now to FIG. 5, a diagram of various components is shown in accordance with some embodiments of the invention. The external system includes a central processing unit (CPU) 705 or processor, which may include a conventional microprocessor, random access memory (RAM) 710 for temporary storage of information, and read only memory (ROM) 715 for permanent storage of information. A memory controller 720 is provided for controlling system RAM 710. A bus controller 725 is provided for controlling data bus 730, and an interrupt controller 735 is used for receiving and processing various interrupt signals from the other system components.

In some embodiments mass storage can be provided by diskette drive 741, which is connected to bus 730 by controller 740, CD-ROM drive 746, which is connected to bus 730 by controller 745, and hard disk drive 751, which is connected to bus 730 by controller 750. User input to the programmer system may be provided by a number of devices. For example, a keyboard and mouse can connected to bus 730 by keyboard and mouse controller 755. DMA controller 760 is provided for performing direct memory access to system RAM 710. A visual display is generated by a video controller 765 or video output, which controls video display 770. The external system can also include a telemetry interface 790 or telemetry circuit which allows the external system to interface and exchange data with an implantable medical device. This description of elements is only provided by way of example and it will be appreciated that some embodiments may lack various elements illustrated in FIG. 7. For example, some embodiments of external devices may lack a diskette drive 741.

Figure 6:
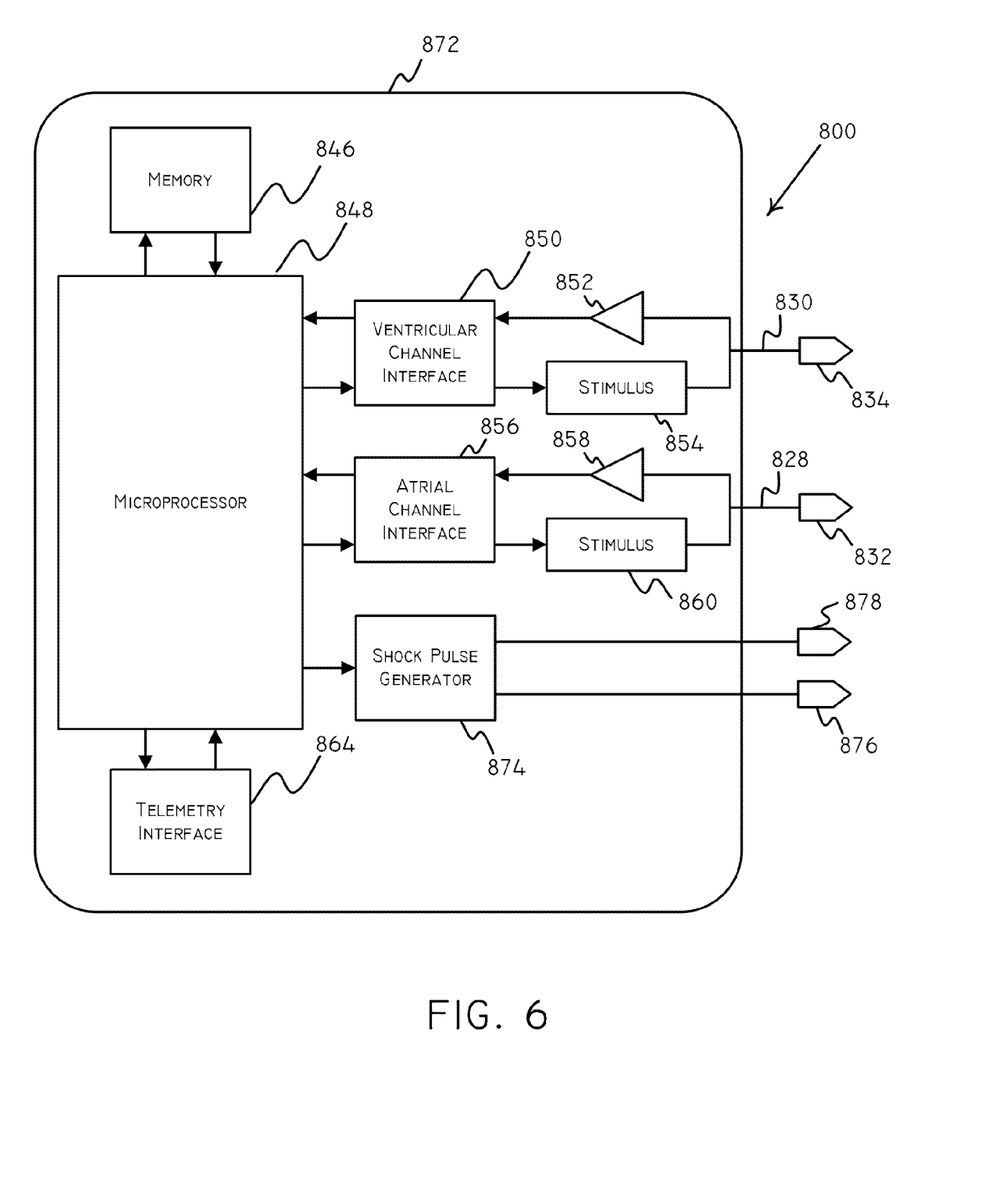
FIG. 6 is a schematic diagram of various components of an implantable device in accordance with some embodiments of the invention.

In some embodiments, one or more operations described above can be executed by an implantable medical device. Referring now to FIG. 6, some components of an exemplary implantable device 800 are schematically illustrated. The implantable medical device 800 can include a controller module 872 coupled to one or more stimulation leads 830 and 828. The controller module 872 can include a microprocessor 848 (or processor) that communicates with a memory circuit (module) 846 via a bidirectional data bus. The memory circuit 846 can include ROM or RAM for program storage and ROM (such as EEPROM) or RAM for data storage. The controller module 872 can be configured to execute various operations such as processing of signals and execution of methods as described herein. A telemetry interface 864 is also provided for communicating with an external unit, such as a programmer device or a patient management system.

The controller module 872 can include ventricular sensing and pacing channels including sensing amplifier 852, output circuit 854, and a ventricular channel interface 850 which communicates bidirectionally with a port of microprocessor 848. It will be appreciated that in some embodiments some of the elements of the controller module 872 shown in FIG. 6 may be omitted. Further, in some embodiments, additional elements may be included.

The ventricular sensing and pacing channel can be in communication with stimulation lead 830 and electrode 834. The controller module 872 can include atrial sensing and pacing channels including sensing amplifier 858, output circuit 860, and an atrial channel interface 856 which communicates bidirectionally with a port of microprocessor 848. The atrial sensing and pacing channel can be in communication with stimulation lead 828 and electrode 832. For each channel, the same lead and electrode can be used for both sensing and pacing. The channel interfaces 850 and 856 can include analog-to-digital converters for digitizing sensing signal inputs from the sensing amplifiers and registers which can be written to by the microprocessor in order to output pulses, change the pacing pulse amplitude, and adjust the gain and threshold values for the sensing amplifiers. A shock pulse generator 874 can also be interfaced to the microprocessor for delivering defibrillation shocks to the heart via a separate pair of electrodes 876, 878. In some embodiments, electrodes 876 and 878 can be disposed along stimulation lead 830 and stimulation lead 828 respectively. In some embodiments, one or more of these components may be omitted. By way of example, if the implantable medical device is a pacemaker, then it may not include a shock pulse generator 874. Similarly, depending on the type of the device and its configuration, it may have a greater or lesser number of electrodes and channels.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method for detecting arrhythmia in a patient comprising:
   sensing concentrations of endothelin-1 in a patient;
   selecting a level of stringency to be used in an arrhythmia detection module based on the sensed concentrations of endothelin-1;
   sensing electrical signals in the patient; and
   evaluating the sensed electrical signals for indicia of an arrhythmia using the arrhythmia detection module.

2. The method of claim 1, wherein selecting the level of stringency comprises decreasing the stringency of the arrhythmia detection module if the concentration of CT-proET-1 is greater than about 104 pmol/L.

3. The method of claim 1, wherein sensing concentrations of endothelin-1 is carried out a plurality of times over a time period greater than one month, the method further comprising calculating a predictive marker trend, wherein selecting the level of stringency comprises decreasing the stringency of the arrhythmia detection module if the predictive marker trend shows that endothelin-1 levels are increasing over time.

4. The method of claim 3, wherein selecting the level of stringency comprises decreasing the stringency of the arrhythmia detection module if the predictive marker trend shows that endothelin-1 levels have increased by at least two standard deviations within one month.

5. The method of claim 1, wherein selecting the level of stringency comprises increasing the stringency of the arrhythmia detection module if the concentration of CT-proET-1 is less than about 66.6 pmol/L.

6. The method of claim 1, wherein the arrhythmia detection module is configured to evaluate one or more of sensed rate, arrhythmia duration, and rhythm morphology.

7. The method of claim 1, wherein selecting the level of stringency to be used in an arrhythmia detection module comprises selecting a risk category based on the endothelin-1 concentration.

8. The method of claim 1, wherein selecting a level of stringency to be used in an arrhythmia detection module including modulating a sensed rate parameter.

9. The method of claim 1, wherein selecting a level of stringency to be used in an arrhythmia detection module including modulating an arrhythmia duration parameter.

10. The method of claim 1, wherein selecting a level of stringency to be used in an arrhythmia detection module including modulating a rhythm morphology parameter.

* * * * *

SEQUENCE LISTING

```
<160> NUMBER OF SEQ ID NOS: 4

<210> SEQ ID NO 1
<211> LENGTH: 212
<212> TYPE: PRT
<213> ORGANISM: Homo sapiens

<400> SEQUENCE: 1

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Asn Pro Ser Arg Glu Arg Tyr Val Thr His Asn
        195                 200                 205

Arg Ala His Trp
    210

<210> SEQ ID NO 2
<211> LENGTH: 38
<212> TYPE: PRT
```

```
<213> ORGANISM: Homo sapiens

<400> SEQUENCE: 2

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 3
<211> LENGTH: 21
<212> TYPE: PRT
<213> ORGANISM: Homo sapiens

<400> SEQUENCE: 3

Cys Ser Cys Ser Ser Leu Met Asp Lys Glu Cys Val Tyr Phe Cys His
1               5                   10                  15

Leu Asp Ile Ile Trp
            20

<210> SEQ ID NO 4
<211> LENGTH: 45
<212> TYPE: PRT
<213> ORGANISM: Homo sapiens

<400> SEQUENCE: 4

Arg Ser Ser Glu Glu His Leu Arg Gln Thr Arg Ser Glu Thr Met Arg
1               5                   10                  15

Asn Ser Val Lys Ser Ser Phe His Asp Pro Lys Leu Lys Gly Asn Pro
            20                  25                  30

Ser Arg Glu Arg Tyr Val Thr His Asn Arg Ala His Trp
        35                  40                  45
```